United States Patent
Ku (10) Patent No.: US 10,533,311 B2
(45) Date of Patent: Jan. 14, 2020

(54) TOILET BOWL WATER STERILIZATION DEVICE AND METHOD THEREFOR

(71) Applicant: Kyo Pil Ku, Seoul (KR)

(72) Inventor: Kyo Pil Ku, Seoul (KR)

( * ) Notice: Subject to any disclaimer, the term of this patent is extended or adjusted under 35 U.S.C. 154(b) by 0 days.

(21) Appl. No.: 15/750,112

(22) PCT Filed: Jul. 27, 2016

(86) PCT No.: PCT/KR2016/008177
§ 371 (c)(1),
(2) Date: Feb. 2, 2018

(87) PCT Pub. No.: WO2017/023007
PCT Pub. Date: Feb. 9, 2017

(65) Prior Publication Data
US 2018/0216331 A1    Aug. 2, 2018

(30) Foreign Application Priority Data

Aug. 6, 2015 (KR) .................. 10-2015-0111108
Jun. 1, 2016 (KR) .................. 10-2016-0068250

(51) Int. Cl.
| E03D 9/03 | (2006.01) |
| A61L 2/03 | (2006.01) |
| A61L 2/10 | (2006.01) |
| A61L 2/24 | (2006.01) |
| A61L 2/28 | (2006.01) |
| E03D 9/02 | (2006.01) |

(52) U.S. Cl.
CPC .............. *E03D 9/037* (2013.01); *A61L 2/035* (2013.01); *A61L 2/10* (2013.01); *A61L 2/24* (2013.01); *A61L 2/28* (2013.01); *A61L 2202/11* (2013.01); *A61L 2202/14* (2013.01)

(58) Field of Classification Search
CPC ........................................ E03D 9/037
USPC ............................................ 4/491
See application file for complete search history.

(56) References Cited

FOREIGN PATENT DOCUMENTS

| JP | 2000080700 A | 3/2000 |
| JP | 2012207456 A | 10/2012 |
| KR | 2020010014373 | 5/2001 |
| KR | 20100023691 A | 3/2010 |
| KR | 1020110030131 A | 3/2011 |
| KR | 1020120047381 A | 5/2012 |
| KR | 1020140142428 A | 12/2014 |

*Primary Examiner* — Lori L Baker
(74) *Attorney, Agent, or Firm* — Levenfeld Pearlstein, LLC (57) ABSTRACT

A toilet bowl water sterilization device and a method therefor, which may electrolyze toilet bowl water stored in a toilet bowl water tank or a pipe, convert the toilet bowl water into electrolyzed water suitable for sterilization and cleaning through the electrolyzing, and sterilize various bacteria which live in a toilet bowl as well as the toilet bowl water tank or the pipe without using a toilet bowl cleaning agent, such as a chemical substance or a surfactant.

12 Claims, 5 Drawing Sheets

TOILET BOWL WATER STERILIZATION DEVICE AND METHOD THEREFOR

BACKGROUND OF THE INVENTION.

The present invention relates to a toilet bowl water sterilization device and a method thereof, and more specifically to, a toilet bowl water sterilization device and a method thereof which may electrolyze toilet bowl water staying in toilet bowl water tanks or pipes so as to convert the toilet bowl water into electrolyzed water suitable for sterilization and cleaning, and sterilize various kinds of bacteria living in each part of a toilet bowl as well as a toilet bowl water tank by using the electrolyzed water, without using a toilet bowl cleaning agent, such as a chemical substance or a surfactant, thereby providing an environment that is clean and pleasant to the user and that is non-toxic to the human body.

Recently, thanks to advanced industrial technologies, toilet bowls (water closets) have been widely distributed and popularized, and against this backdrop, there has been growing interest in sanitation of the toilet and the bathroom having a toilet bowl.

In general, a toilet bowl has a toilet bowl seat on which the user sits to urinate and defecate, and a toilet bowl seat cover for covering the toilet bowl seat, and has a structure in which the toilet bowl is combined with a toilet bowl water tank for storing toilet bowl water used to clean the toilet bowl after urination and defecation.

Furthermore, since tap water that is not sterilized is used to clean the toilet bowl, numerous bacteria invisible to the naked eyes live in the toilet bowl water tank, and each part of the toilet bowl provides an environment where various bacteria may breed due to urination, defecation and moisture.

In particular, whenever the toilet bowl flushes after urination and defecation, all kinds of pathogenic bacteria spreading seriously contaminate the bathroom and the toilet.

In addition, since a toilet bowl installed in the bathroom or the toilet in houses, or installed in the toilet in public places is used by many people, it is highly likely that the toilet bowl is exposed to various pathogenic bacteria causing a variety of illnesses such as skin inflammation, inflammation of the gastrointestinal tract or food poisoning.

To prevent bacterial infection, toilet bowls need to be cleaned on a regular basis and stay clean, and more importantly, toilet bowl water where various bacteria breed needs to be sterilized. In addition, it is important to change toilet bowl water regularly, because bacteria may easily breed in toilet bowl water when toilet bowl water stagnates for a long time.

To clean toilet bowls, toilet bowl cleaning agents are used. They are used by means of a particular device for emitting a certain amount of the toilet bowl cleaning agents, and the device for using the toilet bowl cleaning agents is divided into a submerged type that is put into a toilet bowl water tank, a hung type that is hung directly on a toilet bowl or an attached type that is attached to a toilet bowl, depending on the way that the device is used.

The method of using toilet bowl cleaning agents has a limit in perfectly sterilizing toilet bowl water because a certain amount of the cleaning agents emitted through a nozzle or a pipe through which toilet bowl water passes, at the same time as when the toilet bowl flushes after urination and defecation to sterilize the toilet bowl water, and in this way, the toilet bowl water is not directly sterilized, and only the parts that are contacted are sterilized when the toilet bowl flushes.

Furthermore, as toilet bowl cleaning agents are manufactured with a variety of synthesized chemical substances to improve the ability to sterilize bacteria, in case the body of the user is exposed to the toilet bowl cleaning agents, serious damages such as burns, inflammations or sight loss are caused, and a very unpleasant smell is also caused.

Furthermore, the toilet bowl cleaning agents necessary for being replaced with new ones on a regular basis cause inconvenience and incur additional costs to the user.

Under the circumstances, the present invention is to provide a device and method thereof, wherein toilet bowl water stored in a toilet bowl water tank is electrolyzed by means of electrical electrodes, is converted into electrolyzed water having sterilizing and cleaning abilities to sterilize the toilet bowl water tank, and at the same time, when the toilet bowl flushes, the toilet bowl water tank, the pipe and the toilet bowl may be automatically sterilized.

In the following description, the related arts to which the present invention pertains will be briefly described, and the technical features of the present invention different from those of the related arts will be described.

First of all, Korean Laid-Open Patent Publication No. 2011-0131898 relates to a bidet performing a sterilization function by using Ultraviolet Light Emitting Diode (UV-LED), wherein the bidet has a plurality of UVLED modules and operates the plurality of UVLED modules to sterilize a toilet seat, the inside of a toilet bowl and cleaning water with ultraviolet rays in particular circumstances (e.g. when a person sits on the toilet bowl), or regularly.

The above-described related art is, in part, similar to the present invention in sterilizing toilet bowl water by using ultraviolet rays, but does not describe or suggest the technical features of the present invention that toilet bowl water stored in a toilet bowl water tank is electrolyzed and converted into electrolyzed water having sterilizing and cleaning abilities to clean and sterilize the toilet bowl water tank and the toilet bowl, thereby providing a clean environment to the user.

Furthermore, Korean Laid-Open Patent Publication No. 2010-0023691 (Mar. 4, 2010) relates to a method for automatically cleaning a bidet and a toilet bowl with a device for cleaning a toilet bowl, wherein the method for automatically cleaning a bidet and a toilet bowl with a device for cleaning a toilet bowl is directed to preventing waste of a cleaning agent, whereby a different amount of a cleaning agent is provide to a toilet bowl depending on the functions of a bidet, a drier or a sterilizer after determining which one of the functions is performed when a sensor for sensing the user sits on a seat senses that the user sits on the seat.

The above-described related art is, in part, similar to the present invention in automatically cleaning a toilet bowl, but different from the present invention in that it needs a cleaning agent separately and as a result, incurs costs of purchasing the cleaning agent, and as such a cleaning agent contains a variety of synthesized chemical substances, in case the skin, eyes or mouth of the user are exposed to the agent, the cleaning agent is very harmful to the human body.

On the contrary, the present invention is effective in that it electrolyzes toilet bowl water by means of electrolysis convert the toilet bowl water into electrolyzed water that causes no harm to the human body, and cleans and sterilizes a toilet bowl water tank and a toilet bowl by using the electrolyzed water having sterilizing and cleaning abilities, thereby preventing bacteria in the toilet and the bathroom from breeding.

BRIEF SUMMARY OF THE INVENTION

The present invention is devised to solve the above-described problems and one embodiment of the present invention is directed to providing a toilet bowl water sterilization device and method thereof which may electrolyze toilet bowl water temporarily staying or stored in a toilet bowl water tank or a pipe, convert the toilet bowl water into electrolyzed water to sterilize the toilet bowl water as well as the toilet bowl water tank and each part of a toilet bowl without using a cleaning agent or other compounds.

Furthermore, one embodiment of the present invention is directed to providing a toilet bowl water sterilization device and method thereof which may electrolyze the toilet bowl water stored in the toilet bowl water tank or the pipe by means of a device of aqua plasma for generating microbubbles and OH radicals such that the electrolyzed toilet bowl water may have a stronger sterilizing ability.

Furthermore, one embodiment of the present invention is directed to providing a toilet bowl water sterilization device and method thereof which may sterilize the toilet bowl water by means of electrolysis, ultraviolet rays or combination thereof, may prevent the user of the toilet bowl from being infected with pathogenic bacteria, and may block in advance spread of bacteria that happens when the toilet bowl water is discharged to clean urine and faces, thereby providing an environment that is clean and pleasant to the user.

Furthermore, one embodiment of the present invention is directed to sterilizing the toilet bowl water tank, the pipe or the toilet bowl by means of the electrolyzed water without using a cleaning agent or other compounds, thereby resulting in a significant reduction in additional costs incurred for disposing of waste caused by the cleansing agent or other compounds and incurred for repurchasing the cleaning agent or other compounds regularly, and providing convenience to the user.

Furthermore, one embodiment of the present invention is directed to maximizing efficiency of the electrolysis whereby the toilet bowl water sterilization device inside the toilet bowl water tank provides electrolytes to the toilet bowl water, or electrolytes are added to water flowing from a tap water pipe of the outside by means of an electrolyte supply control valve to provide the water added with the electrolytes directly into the toilet bowl water tank.

Furthermore, one embodiment of the present invention is directed to providing convenience to the user, wherein the toilet bowl water sterilization device may be controlled, or the state where the toilet bowl sterilization device operates, information on bacteria inside the toilet bowl water tank, the state of being sterilized, or combination thereof may be monitored by means of a control module installed at the exterior of the toilet bowl water tank according to the present invention.

Furthermore, one embodiment of the present invention is directed to providing convenience to the user wherein the user may control the toilet bowl water sterilization device remotely by means of communication networks, or the state where the toilet bowl sterilization device operates, information on bacteria inside the toilet bowl water tank, the state of being sterilized, or combination thereof may be provided to a terminal of the user.

A toilet bowl water sterilization device according to the present invention comprises an electrolyzed water sterilization unit for converting toilet bowl water in a toilet bowl including a urinal, a closet bowl, a water closet or a bidet into electrolyzed water by means of electrolysis to sterilize the toilet bowl water, and a control module to set conditions for converting the toilet bowl water into electrolyzed water in the electrolyzed water sterilization unit, to control the operation of sterilizing the t bowl water, to monitor the state of the toilet bowl water, or to perform combination thereof.

Furthermore, the electrolysis is performed whereby electrolytes including salt, potassium or combination thereof are added to the toilet bowl water, and the electrolytes are added inside a toilet bowl water tank, added through a tap water pipe provided with the toilet bowl water, or added through link thereof.

Furthermore, the toilet bowl water sterilization device further comprises an ultraviolet sterilization unit for radiating ultraviolet rays into the toilet bowl water tank to sterilize the toilet bowl water.

Furthermore, the electrolyzed water sterilization unit further comprises sterilizing the toilet bowl water by means of a device of aqua plasma using catalysts.

Furthermore, the toilet bowl water sterilization device further comprises a bacterium sensing unit for sensing bacteria in the toilet bowl water, wherein information on the state of the toilet bowl water including kinds of bacteria, the number of bacteria, levels of contamination of the toilet bowl water, whether the sterilization is performed or not, or combination thereof collected by the bacterium sensing unit is provided to the control module.

Furthermore, the control module further comprises an information display unit for displaying the state where the toilet bowl water sterilization device operates, information on the state of the toilet bowl water, or combination thereof.

Furthermore, the control module further comprises a communication interface unit for providing a communication environment including a wired one, a wireless one, or combination thereof, wherein interfaces are provided to transmit the information on the state of the toilet bowl water to the outside, or to control the operation of the toilet bowl water sterilization device from the outside.

In addition, a method of sterilizing toilet bowl water according to one embodiment of the present invention comprises control steps of setting conditions for converting toilet bowl water in a toilet bowl including a urinal, a closet bowl, a water closet or a bidet into electrolyzed water by means of electrolysis, of controlling the operation of sterilizing the toilet bowl water, of monitoring the state of the toilet bowl water, or of performing combination thereof, and sterilization steps of sterilizing the toilet bowl water in the toilet bowl water tank by means of ultraviolet rays radiated, or of sterilizing the toilet bowl water in the toilet bowl water by means of electrolyzed water, converted from the toilet bowl water, having sterilizing and cleansing abilities.

Furthermore, electrolysis of the toilet bowl water is carried out, whereby electrolytes including salt, potassium, or combination thereof are added to the toilet bowl water to electrolyze the toilet bowl water, and the electrolytes are added inside the toilet bowl water tank, added through a tap water pipe provided with the toilet bowl water, or added through link thereof.

Furthermore, the sterilization step further comprises sterilizing the toilet bowl water by means of ultraviolet rays radiated, or sterilizing the toilet bowl water by means of the device of aqua plasma using a catalyst.

Furthermore, the method of sterilizing toilet bowl water further comprises sensing bacteria in the toilet bowl water, wherein information on the state of the toilet bowl water including kinds of bacteria, the number of bacteria, levels of contamination of the toilet bowl water, whether the sterilization is performed or not, or combination thereof is collected to be provided to a terminal of the user.

Furthermore, the method of sterilizing toilet bowl water further comprises displaying information on the state where the toilet bowl water sterilization device operates, the state of the toilet bowl water or combination thereof.

As described above, a toilet bowl water sterilization device and method thereof according to the present invention are effective in that toilet bowl water stored in a toilet bowl water tank and a pipe is converted into electrolyzed water that causes no harm to the human body and has a strong sterilizing ability to sterilize and clean the toilet bowl water tank and a toilet bowl without using a cleaning agent that is a chemical compound.

Furthermore, the present invention is effective in that secondary contamination caused by spread of bacteria may be prevented because toilet bowl water itself used to clean a toilet bowl after urination and defecation is converted into electrolyzed water having a sterilizing ability.

Furthermore, the present invention is effective in that costs of sterilizing a toilet bowl are not incurred, and unlike cleaning agents for toilet bowls manufactured from compounds consisting of chemical substances, costs of disposing of the waste that causes environmental pollution are not incurred because the present invention cleans and sterilizes a toilet bowl by using toilet bowl water.

Furthermore, the present invention is effective in that the technology of aqua plasma is applied to electrolyze toilet bowl water stored in a toilet bowl water tank and in this way, microbubbles and OH radicals are generated such that the electrolyzed toilet bowl water may have a stronger sterilizing ability.

Furthermore, the present invention is effective in that it may sterilize toilet bowl water by means of electrolysis, ultraviolet rays or combination thereof, may prevent the user of a toilet bowl from being infected with pathogenic bacteria and block spread of bacteria that happens when toilet bowl water is discharged to clean urine and faces, thereby providing an environment that clean and pleasant to the user.

Furthermore, the present invention is effective in that the toilet bowl water sterilization device may be controlled, or the state where the toilet bowl water sterilization device operates, information on bacteria in a toilet bowl water tank, the state of being sterilized or combination thereof may be monitored so as to provide convenience to the user.

Furthermore, the present invention is effective in that the user may remotely control the toilet bowl water sterilization device means of communication networks, or information on the state where the toilet bowl sterilization device operates, bacteria inside a toilet bowl water tank, the state of being sterilized, or combination thereof may be provide to a terminal of the user, so as to provide convenience to the user.

DETAILED DESCRIPTION OF THE INVENTION

Below, by describing the preferred embodiments of the present invention with reference to the accompanying drawings, the present invention will be described in detail. Like reference numerals in each drawing denote like members.

Hereunder, with reference to FIGS. 1 and 2, a toilet bowl water sterilization device 10 will be described in detail.

Figure 1:
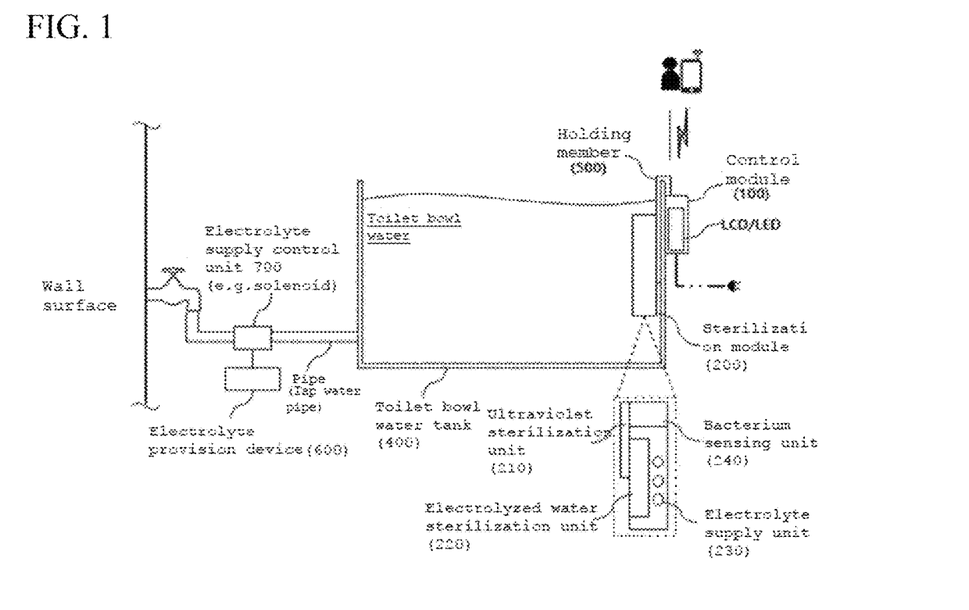
FIG. 1 is a conceptual diagram of illustrating a toilet bowl water sterilization device according to one embodiment of the present invention.
Figure 2:
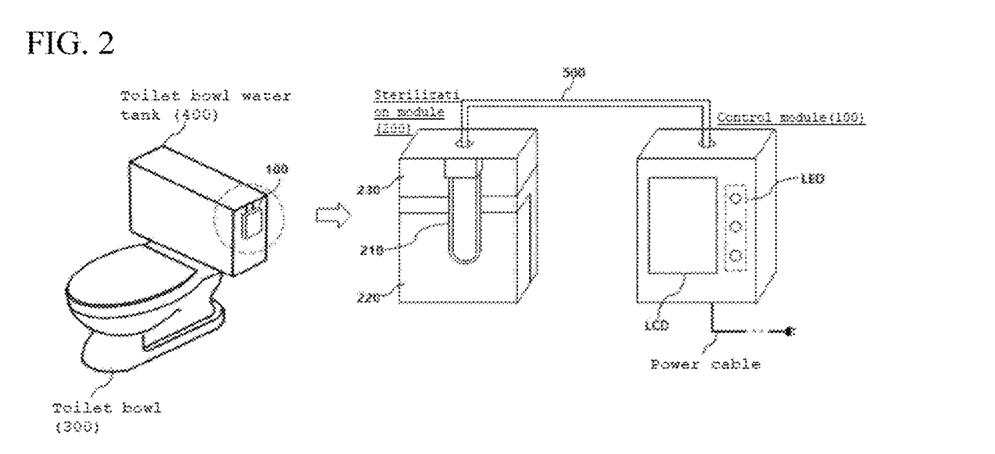
FIG. 2 is a view illustrating a configuration of a toilet bowl water sterilization device according to one embodiment of the present invention.

FIG. 1 is a conceptual diagram illustrating a toilet bowl water sterilization device according to one embodiment of the present invention, and FIG. 2 is a view illustrating a configuration of a toilet bowl water sterilization device 10 according to one embodiment of the present invention.

As illustrated in FIGS. 1 and 2, a toilet bowl water sterilization device 10 is configured to comprise a sterilization module 200 for sterilizing toilet bowl water used for a toilet bowl and a control module 100 for automatically controlling the sterilization module 200.

Furthermore, the toilet bowl water sterilization device 10 is held on one side of a toilet bowl water tank by means of a holding member 500 (e.g cradle) to perform a series of steps for sterilizing toilet bowl water.

Furthermore, the control module 100 and the sterilization module 200 are electrically connected by means of a connecting cable inside the holding member 500.

Meanwhile, the toilet bowl 300 means a water closet, in which urine and faces are cleaned by water, includes toilet bowls or squat toilets, which are in combination with a toilet bowl water tank 400 storing toilet bowl water used to wash out urine, faces and a toilet bowl.

Furthermore, the sterilization module 200 composing the toilet bowl water sterilization device 10 is placed inside the toilet bowl water tank 400 and installed in the toilet bowl water tank 400 in the state of being submerged in the toilet bowl water stored in the toilet bowl water tank 400.

Furthermore, the control module 100 is configured to comprise an ultraviolet sterilization unit 210 for sterilizing the toiler bowl water by radiating ultraviolet rays into the toilet bowl water tank 400, an electrolyzed water sterilization unit 220 for electrolyzing the toilet bowl water stored in the toilet bowl water tank 400 to convert it into electrolyzed water having sterilizing and cleaning abilities, an electrolyte supply unit 230 for adding electrolytes to the toilet bowl water to improve efficiency of the electrolysis and a bacterium sensing unit 240 for sensing information on the state of the toilet bowl water.

Meanwhile, with reference to FIG. 3, each component composing the control module 100 will be described in detail.

Furthermore, the control module 100 is placed outside the toilet bowl water tank 400 and electrically connected with the sterilization module 200 to control the sterilization module 200.

Preferably, the toilet bowl water sterilization device 10 is installed on one side of the toilet bowl water tank 400, but may be installed on a cover covering the toilet bowl water tank 400. Furthermore, the sterilization module 200 may be fixed on one side of the interior of the toilet bowl water tank 400, or may be installed in the state of floating on the toilet bowl water (For instance, when the toilet bowl water levels are low, the sterilization module 200 goes down to a specific water level and it does not go further down and it hangs in the air by means of the connecting cable with a certain length connected to the control module 100, in case it is installed in the state of floating on the toilet bowl water.). That is, as long as the sterilization module 200 and the control module 100 are placed inside and outside the toilet bowl water tank 400 respectively to perform functions of their own, they may be placed in various locations of the toilet bowl 300 in various ways. Furthermore, the toilet bowl water sterilization device 10 may be used in connection with a home automation system, and then, functions of the control module 100 may be performed in the home automation system.

Furthermore, the control module 100 controls the sterilization module 200 to sterilize the toilet bowl water and to convert the toilet bowl water into water that causes no harm to the human body, such that the toilet bowl water may be electrolyzed. As a result of the electrolysis, the toilet bowl water is converted into electrolyzed water.

As the electrolyzed water causes no harm and is non-toxic to the human body and has strong sterilizing and cleaning abilities, the toilet bowl water itself may be sterilized and cleaned with no need to use cleaning agents for toilet bowls or germicides for toilet bowls.

Furthermore, by means of the electrolyzed water, the toilet bowl water tank 400 may be sterilized and cleaned, and when the toilet bowl water emits, the toilet bowl (in particular, the inside of the toilet bowl where the toilet bowl water left after cleaning urination and defecation stagnates) may also be sterilized and cleaned.

Such features of the present invention are helpful to prevent illnesses caused by bacteria and to prevent bacteria from breeding because the toilet bowl water itself used to clean urination and defecation has sterilizing and cleaning abilities.

However, as the electrolyzed water converted by means of electrolysis has the feature that when it is exposed to sunlight or air for a long period of time, it loses the features as electrolyzed water. As a result, the present invention performs the electrolysis of the toilet bowl water in the toilet bowl water tank 400 according to a preset time regularly.

Meanwhile, the present invention automatically adds electrolytes, a material having a high degree of ionization, such as potassium or salt to the toilet bowl water to maximize the efficiency of the electrolysis.

Electrolytes having a high degree of ionization such as the salt or the potassium are mixed with the toilet bowl water and separated into positive ions and negative ions nearly 100% in the process of electrolyzing the toilet bowl water, and as a result, they facilitates current flow, minimizes resistance against current, and improves the efficiency in the electrolysis.

Furthermore, the electrolytes are added directly to the toilet bowl water by an electrolyte supply unit 230 installed in the sterilization module 200. Furthermore, the electrolytes may be added through a tap water pipe provided with the toilet bowl water, and then, the toilet bowl water provided to the toilet bowl water tank 400 is in the state where the electrolytes are added.

Furthermore, in the case where electrolytes are added through the tap water pipe, the toilet bowl water sterilization device 10 is linked with an electrolyte supply control valve 700 installed in a part of the tap water pipe such that the electrolytes may be automatically added to the toilet bowl water when the toilet bowl water flows into the toilet bowl water tank 400 through the tap water pipe.

The electrolyte supply control valve 700 is connected with an electrolyte provision device 600 for storing and providing electrolytes, and normally keeps the tap water pipe and a connection passage for providing electrolytes to the tap water pipe from the electrolyte provision device 600, respectively locked up. Then, when receiving the instructions for unlocking the tap water pipe and the connection passage from the toilet bowl water sterilization device 10, the electrolyte supply control valve 700 opens the tap water pipe and the connection passage simultaneously such that the electrolytes provided by the electrolyte provision device 600 may be added to the toilet bowl water flowing into the toilet bowl water tank 400.

Furthermore, when receiving the instructions for locking the tap water pipe and the connection passage from the toilet bowl sterilization device 10, the electrolyte supply control valve 700 locks the tap water pipe and the connection passage.

Meanwhile, when the user flushes the toilet bowl after urination and defecation, the instructions for unlocking the tap water pipe and the connection passage are given, from the toilet bowl water sterilization device 10 to the electrolyte supply control valve 700, to control the electrolyte supply control valve 700, such that new toilet bowl water may flow in and be stored in the toilet bowl water tank 400, and when enough toilet bowl water flows into the toilet bowl water tank 400, the instructions for locking the tap water pipe and the connection passage are given to lock the tap water pipe and the connection passage.

Furthermore, the electrolyte supply control valve 700 may be configured to be a solenoid valve, and the solenoid valve is used to control the flow of gas or fluid in the way of being totally closed or totally open. The solenoid valve is effective in that it may automatically perform lock and unlock functions according to electric signals or control signals remotely unlike manual valves which are operated to perform lock and unlock functions directly by the user.

Meanwhile, the electrolyzed water converted by the toilet bowl water sterilization device 100 by means of the electrolysis has different properties depending on kinds of the electrolytes added to the toilet bowl water. In the case where the electrolytes are salt, the toilet bowl water is converted into electrolyzed water having acidity levels high or low enough to have sterilizing abilities, and in the case where the electrolytes are potassium, the toilet bowl water is converted into electrolyzed water having alkalinity levels high enough to have sterilizing and cleaning abilities. As described above, the electrolyzed water has different properties depending on kinds of electrolytes used when the toilet bowl water is electrolyzed. However, the present invention does not limit the kinds of the electrolytes used for the electrolysis because the present invention is directed to sterilizing the toilet bowl water, the toilet bowl water tank 400 and the toilet bowl 300 thereby providing a clean environment to the user.

As a result, the electrolyzed water converted from the toilet bowl water by means of the electrolysis causes no harm, is non-toxic to the human body and is replaceable with traditional toilet bowl cleaning agents, is highly useful to prevent environmental pollution and does not incur additional costs of sterilizing and cleaning the toilet bowl water tank 400 or the toilet bowl 300.

Furthermore, the toilet bowl water sterilization device radiates ultraviolet rays with appropriate wavelengths existing in the toilet bowl water to the toilet bowl water to sterilize bacteria existing in the toilet bowl water.

As described above, the toilet bowl water sterilization device 10 not only sterilizes bacteria in the toilet bowl water by continuously radiating the ultraviolet rays to the toilet bowl water, but also sterilizes the toilet bowl water by using the electrolyzed water converted by means of the electrolysis, thereby providing the electrolyzed water that causes no harm and is non-toxic to the human body and has a strong sterilizing ability.

Furthermore, the technology of aqua plasma is applied to the toilet bowl water sterilization device 10 to electrolyze the toilet bowl water, thereby converting the toilet bowl water into the electrolyzed water having strong sterilizing and cleaning abilities.

By means of the technology of aqua plasma, the toilet bowl water gets into the state of plasma and ionizes, and then, the ionized toilet bowl water generates microbubbles and OH radicals. The OH radicals, a natural material as well as an environmentally friendly material, existing in the natural environment, are capable of suppressing the breeding of almost all of the bacteria and viruses in the toilet bowl water, and carrying out decomposition of materials having a chemically combined structure such as heavy metals or pesticides so as to turn such materials into the ones that cause no harm to the human body.

Furthermore, the microbubbles are bubbles invisible to the naked eyes, and the microbubbles generated by means of the ionization rise at very low speeds and extinct before reaching the surface of water. Then, heat having a temperature of greater than or equal to 4,000 degrees Celsius is instantly generated such that the bacteria existing in the toilet bowl water may be sterilized.

Furthermore, the toilet bowl water sterilization device 10 may be connected to a terminal of the user such as smart phones, tablets or laptops by means of wireless communication technologies such as WiFi, Bluetooth, 3G or 4G or wired communication technologies.

Furthermore, the user may access the toilet bowl water sterilization device 10 by using applications or software installed in the terminal of the user, and may remotely turn on and off the toilet bowl water sterilization device 10, and may control the electrolysis of the toilet bowl water and the intensity of ultraviolet radiation.

Furthermore, the toilet bowl water sterilization device 10 provides various information including information on the state of the toilet bowl water in the toilet bowl water tank 400, the state where the toilet bowl water sterilization device 10 operates or combination thereof to the terminal of the user real time or regularly, such that the user may monitor the state of the toilet bowl water stored in the toilet bowl water tank 400 and the state where the toilet bowl water sterilization device 10 operates.

The information on the state of the toilet bowl water consists of the number of bacteria existing in the toilet bowl water or the toilet bowl water tank 400, levels of contamination of the toilet bowl water or the toilet bowl water tank 400, whether sterilization is performed or not, kinds of bacteria or combination thereof.

Furthermore, the control module 100 is capable displaying the information on the state of the toilet bowl water and the overall state where the bowl water sterilization device 10 operates by means of LCD and LED. For instance, the number of bacteria, levels of contamination, whether sterilization is performed or not, kinds of bacteria or combination thereof may be displayed as letters, images, numbers or combination thereof by means of LCD, and the colors of LED may be used to visually display the information on the state of the toilet bowl water (e.g. when the number of bacteria is greater than or equal to a certain number, the light turns red, and when the number of bacteria is less than or equal to a certain number, the light turns green.).

Furthermore, the toilet bowl water sterilization device 10 electrolyzes the toilet bowl water regularly according to a preset time schedule such that the toilet bowl water may be kept clean consistently.

Furthermore, the toilet bowl water sterilization device 10 instantly performs the electrolysis to convert the toilet bowl water into the electrolyzed water having sterilizing and cleaning abilities, when a sensing sensor (invisible) senses that the user flushes the toilet bowl after urination and defecation, and new toilet bowl water flows into the toilet bowl water tank 400. Meanwhile, the sensing sensor for sensing the use of the toilet bowl water consists of a sensor for sensing the operation of a toilet lever used to flush the toilet bowl, a sensor for sensing changes in water levels of the toilet bowl water (i.e. sensing that when the toilet flushes, the water level of the toilet bowl water goes down and when new toilet bowl water flows into the toilet bowl water tank, it goes up) or combination thereof.

Furthermore, the bacterium sensing unit 240 may sense the use of the toilet bowl water without having a separate sensing sensor for sensing the use of the toilet bowl water. That is, the electrolyzed water sterilization unit 220 converts the toilet bowl water into the electrolyzed water, and then, in the case where the bacterium sensing unit 240 senses that bacteria exist in the toilet bowl water as a result of sensing the state of the toilet bowl water before a certain period of time elapses to perform another electrolysis, and determines that new toilet bowl water flows in after the toilet bowl water is used, the electrolysis may be performed.

Meanwhile, naturally, the toilet bowl water sterilization device 10 of the present invention is waterproofed to prevent failure caused by moisture infiltrated into the toilet bowl water sterilization device 10 because a toilet bowl 300 is usually installed in places such as the toilet or the bathroom with high humidity levels.

Furthermore, the toilet bowl water sterilization device 10 may consist of plastic that is environmentally friendly and antibacterial such as biodegradable plastic and biomass-based plastic, thereby preventing environmental pollution at the time of disposing of the toilet bowl water sterilization device 10.

Within 1 to 2 years, such plastic that is environmentally friendly and antibacterial has the advantage of completely being degraded by microorganisms or degrading enzymes such as bacteria, algae and fungi existing in the natural environment, and turning into water and carbon dioxide, thereby causing no harm to the environment.

Furthermore, the toilet bowl water sterilization device 10 may be configured to be installed to a bidet provided on a toilet bowl to sterilize cleaning water emitted through the nozzle of the bidet. In addition, the electrolyte supply control valve 700 according to one embodiment of the present invention may be installed to the pipe of a urinal to provide the electrolyzed water to the urinal by means of the electrolyte provision device 600 such that the urinal may be kept hygienic. That is, such an embodiment may be applied not only to a toilet bowl water tank but also installed directly to a branch pipe to sterilize a bidet or a urinal.

Figure 3:
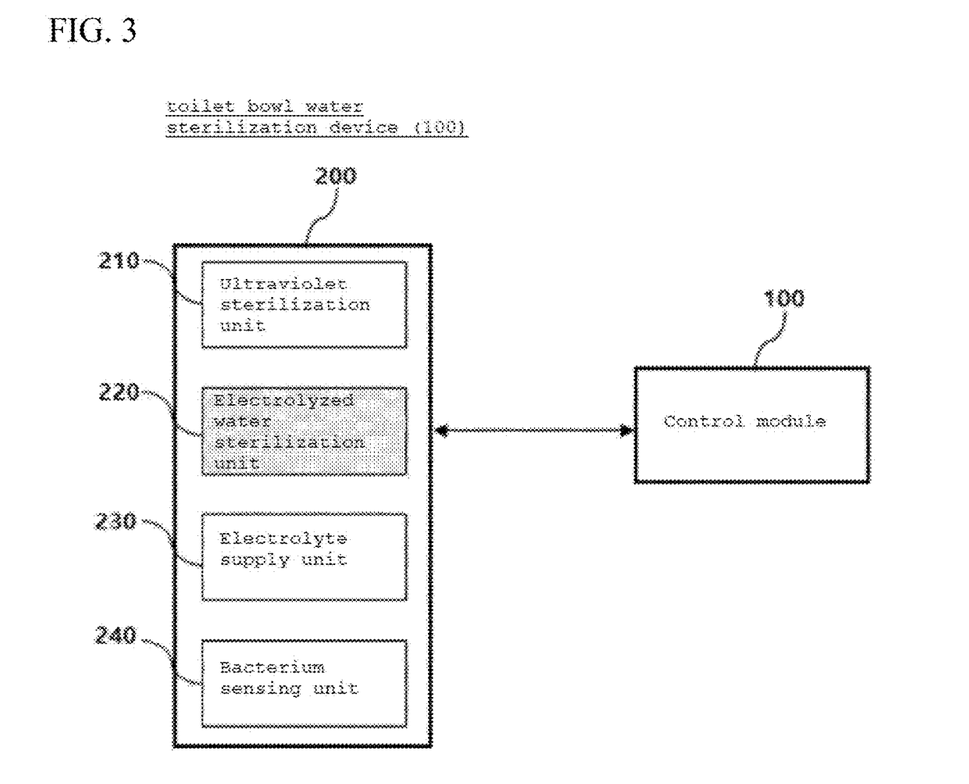
FIG. 3 is a block diagram illustrating a configuration of a sterilization module according to one embodiment of the present invention.

FIG. 3 is a block diagram illustrating a configuration of sterilization module according to one embodiment of the present invention.

As illustrated in FIG. 3, the sterilization module 200 is configured to comprise the ultraviolet sterilization unit 210, placed in the toilet bowl water tank 400, for radiating ultraviolet rays into the toilet bowl water stored in the toilet bowl water tank 400 so as to sterilize the toilet bowl water, the electrolyzed water sterilization unit 220 for converting the toiler bowl water into electrolyzed water by means of electrolysis and for sterilizing the toilet bowl water by using the electrolyzed water, the electrolyte supply unit 230 for providing electrolytes at the time of the electrolysis and the bacterium sensing unit 240 for sensing bacteria existing in the toilet bowl water.

The ultraviolet sterilization unit 210 consists of at least one or more of an ultraviolet sterilizer lamp (invisible), and radiates short-wave ultraviolet rays whose wavelengths may be set to range from 200 nm to 280 nm, and in particular, may radiate ultraviolet rays having wavelengths of 265 nm or 253.7 nm capable of effectively sterilizing bacteria, viruses and fungi.

Furthermore, preferably, the ultraviolet rays are radiated continuously but may be set in advance to operate regularly for a certain period of time (e.g. a 20-minute radiation of the ultraviolet rays is performed every hour.)

Furthermore, the electrolyzed water sterilization unit 220 electrolyzes the toilet bowl water to convert the toilet bowl water into the electrolyzed water, and the electrolysis is performed by direct current added between two electrodes submerged in the toilet bowl water. The Electrolyzed water converted as a result of the electrolysis has properties of acids or strong alkalis.

Furthermore, the electrodes, preferably, are platinum ones to catalyze the electrolysis, but in addition to the platinum electrodes, various catalyst electrodes such as iridium, iron or nickel may be used.

In general, electrolysis is categorized into electrolysis with diaphragm where ion selective diaphragm is installed in a water tank (a tank refers to a tank containing water used for electrolysis, and refers to a toilet bowl water tank in the present invention), and a negative electrode compartment (a part where the negative electrode is placed) and a positive electrode compartment part where the positive electrode is placed) are divided for electrolysis, and electrolysis with non-diaphragm where ion selective diaphragm is not installed for electrolysis.

In the electrolysis with diaphragm, acid water is generated in the negative electrode compartment and alkaline water is generated in the positive electrode compartment. The acid water and alkaline water have strong sterilizing and cleaning abilities, but because the acid water and the alkaline water are mixed and lose their own features thereby immediately returning to the original toilet bowl water when the toilet bowl flushes such that toilet bowl water may used, only 50% of toilet bowl water should be used such that the toilet bowl water have stabilizing and cleaning abilities, and because the acid water and the alkaline water have the features that when they are exposed to sunlight or air for a long period of time, they lose their own features, electrolysis should be often performed.

Meanwhile, when toilet bowl water is converted into electrolyzed water by means of the electrolysis with non-diaphragm, the electrolyzed water may be used 100% because it returns to the original toilet bowl water only when it is exposed to sunlight or air for a long period of time.

Accordingly, the present invention electrolyzes the toilet bowl water stored in the toilet bowl water tank 400 by means of the electrolysis with non-diaphragm so as to maximize efficiency in the use of the electrolyzed water. However, naturally, the electrolysis with diaphragm may be used depending on the place where the toilet bowl water sterilization device 10 is installed, an environment, the structure of a toilet bowl water tank 400, the structure of a toilet bowl etc.

Furthermore, the electrolysis may be performed by means of a device of aqua plasma (invisible), and the device of aqua plasma induces the discharge between two electrodes placed in water (toilet bowl water) and converts the toilet bowl water from fluid to plasma to ionize the toilet bowl water.

The ionized toilet bowl water generates microbubbles and OH radicals, the generated microbubbles and OH radicals are used to sterilize bacteria existing in the toilet bowl water and to degrade materials having the same chemically combined structure as proteins such that such materials may turn into the ones that cause no harm to the human body. By means of this mechanism, the toilet bowl water may have sterilizing and cleaning abilities.

Meanwhile, although the user flushes the toilet bowl to wash away urination and defecation as well as the toilet bowl, a part of toilet bowl water still remains in the toilet bowl. After a certain period of time, bacteria may breed in the remaining toilet bowl water. The toilet bowl water sterilization device 10, connected with a device for emitting toilet bowl water to a toilet bowl (e.g. a device of a bidet for emitting cleaning water, a lever for flushing a toilet bowl), regularly emits the electrolyzed water to the toilet bowl 300 according to a preset time to replace the remaining toilet bowl water, thereby preventing the bacteria from breeding.

Furthermore, the electrolyzed water sterilization unit 220, when the toilet bowl water is electrolyzed, enables the electrolyte supply unit 230 to supply electrolytes to the toilet bowl water such that efficiency in the electrolysis may be maximized. Furthermore, the toilet bowl water sterilization device 10 is connected with the electrolyte supply control valve 700 and the electrolyte provision device 600 installed in the exterior tap water pipe and enables the electrolytes to be added to the toilet bowl water flowing into the toilet bowl water tank 400 such that the efficiency in the electrolysis may be maximized. That is, the toilet bowl water sterilization device 10 adds the electrolytes including salt, potassium or combination thereof to the toilet bowl water to perform the electrolysis, and the electrolytes are added inside the toilet bowl water tank 400 by means of the electrolyte supply unit 230, added through the tap water pipe used for providing the toilet bowl water (then, the electrolytes are added by means of the electrolyte provision device 600), or added through link thereof.

Furthermore, the bacterium sensing unit 240 senses bacteria existing in the toilet bowl water or the toilet bowl water tank 400 and transmit information on the sensed bacteria (the number of bacteria or levels of contamination) to the control module 100 such that the information may be provided to the user.

Meanwhile, when bacteria exist in the toilet bowl water or the toilet bowl water tank 400, the control module 100 controls the ultraviolet sterilization unit 210 or the electrolyzed water sterilization unit 220 to sterilize the bacteria on the basis of the information provided by the bacterium sensing unit 240.

Meanwhile, the electrodes (e.g. platinum electrodes) and the ultraviolet sterilizer lamp used for the electrolysis as a means to sterilize the toilet bowl water don't need to be often replaced with new ones like cleaning agents because once they are installed, they may be used for a very long time (e.g. the life span of the platinum electrodes is greater than or equal to 4 years, the lifespan of the ultraviolet sterilizer lamp is greater than or equal to about 8,000 hours), thereby incurring low costs of operating the toilet bowl water sterilization device 10.

Figure 4:
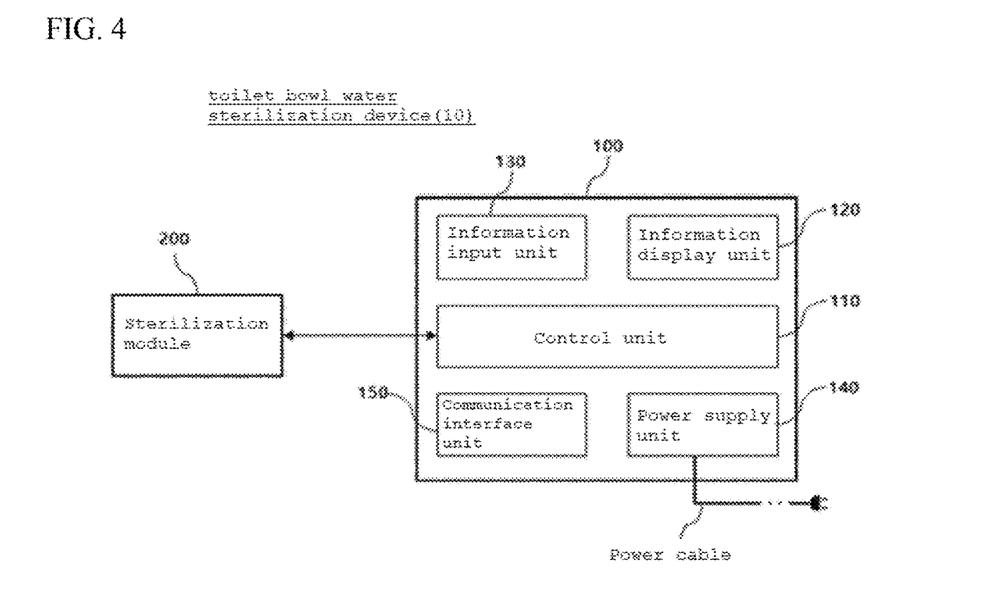
FIG. 4 is a block diagram illustrating a configuration of a control module according to one embodiment of the present invention.

FIG. 4 is a block diagram illustrating a configuration of a control module according to one embodiment of the present invention.

As illustrated in FIG. 4, the control module 100 is configured to comprise a control unit 110 for controlling the sterilization module 200, an information display unit 120 for visually displaying the information on the state of sterilization and bacteria in the toilet bowl water tank 400, an information input unit 130 for inputting details to control the toilet bowl water sterilization device 10, a power supply unit 140 for providing power provided from the outside to the toilet bowl water sterilization device 10, and a communication interface unit 150.

The control unit 110 controls the sterilization module 200 according to the conditions set by the user to sterilize the toilet bowl water stored in the toilet bowl water tank 400 and to sterilize and clean the toilet bowl water tank 400 and the toilet bowl 300 by using the sterilized toilet bowl water.

Furthermore, the control unit 110 exerts overall control such as dataflow of the toilet bowl water sterilization device 10 or the driving between components.

Furthermore, the information input unit 130 receives information input by the user to operate or control the toilet bowl water sterilization device 10, and the control unit 110 controls the control module 100 and the sterilization module 200 according to the information input.

Meanwhile, the information needed to manage or control the toilet bowl water sterilization device 10 comprises setting the time for operating the electrolyzed water sterilization unit 220 in the sterilization module 200 or setting the time for operating the ultraviolet sterilization unit 210.

Furthermore, the time for operating the electrolyzed water sterilization unit 220 or for operating the ultraviolet sterilization unit 210 is set by the user such that the electrolysis of the toilet bowl water and the radiation of the ultraviolet rays may be performed according to the set time, and the control unit 110 controls the sterilization module 200 according to the set time for sterilizing the toilet bowl water.

Furthermore, the information display unit 120 displays the information on the state where the toilet bowl water sterilization device 10 operates, the on and off state of the toilet bowl water sterilization device, the state of toilet bowl water or combination thereof by outputting the information in LCD, LED or combination thereof such that the user may instantly recognize the information.

Furthermore, the power supply unit 140 provides power provided from the outside to the toilet bowl water sterilization device 10 to operate the toilet bowl water sterilization device 10.

Meanwhile, the control module 100 may be configured to further comprise a stabilizer (invisible) for controlling the power provided by the power supply unit 140 constantly to use the toilet bowl water sterilization device 10 in a stable manner.

Furthermore, the control module 100 may be configured to further comprise an over electric current sensor (invisible) for sensing and blocking over electric current that exceeds a fixed amount of electric current caused by a short circuit or other internal and external factors.

The over electric current sensor senses the over electric current that may happen in the control module 100 or the sterilization module 200 and blocks the supply of the power provided from the outside to prevent the damage of the toilet bowl water sterilization device 10 that is caused by the over electric current.

Furthermore, the toilet bowl water sterilization device may be configured to further comprise an air cleaner (invisible) for regularly emitting air cleaning agents or ion fragrances into the air according to the time set by the user so as to remove odor floating in the air in a place installed with the toilet bowl 300 according to the time set by the user, thereby providing a pleasant environment to the user.

Furthermore, the communication interface unit 150 communicates with a terminal of the user, and the user may input information necessary for operating and controlling the toilet bowl water sterilization device 10, or remotely control the toilet bowl water sterilization device 10 to sterilize the water of the toilet bowl water tank 400 by means of the user's terminal.

Furthermore, the user may receive and check a variety of information including the state where the toilet bowl water sterilization device 10 operates, the state of toilet bowl water or combination thereof by means of the communication interface unit 150, and the information may be transmitted to the user on a regular basis or at the request of the user.

Figure 5:
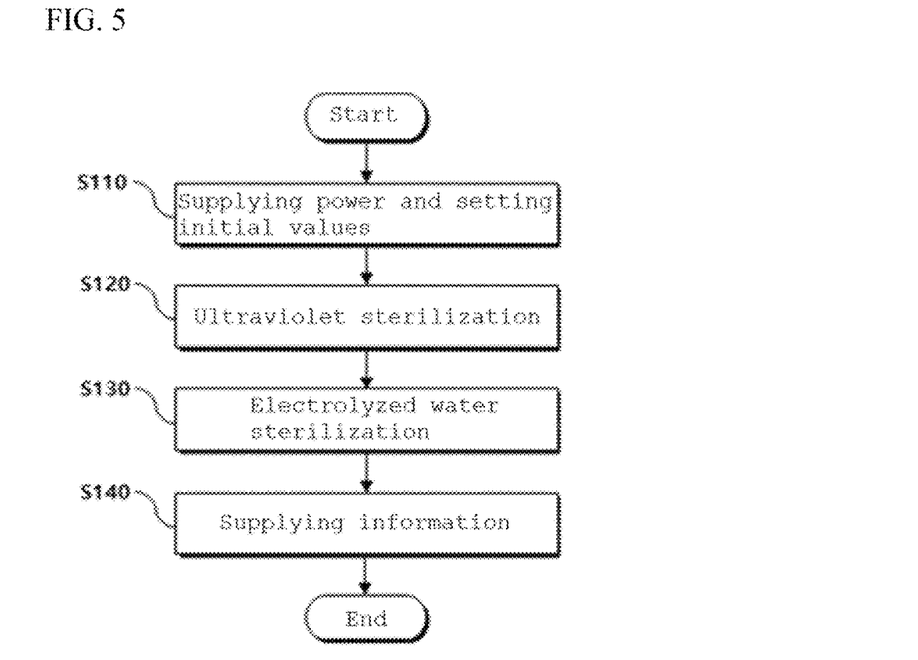
FIG. 5 is a flow chart illustrating steps of sterilizing a toilet bowl water tank according to one embodiment of the present invention.

FIG. 5 is a flow chart illustrating steps of sterilizing a toilet bowl water tank according to one embodiment of the present invention.

As illustrated in FIG. 5, the steps of sterilizing a toilet bowl water tank 400 includes, first, connecting a power cable, provided to a toilet bowl water sterilization device 10, to an external power supply device to operate the toilet bowl water sterilization device 10 installed to a toilet bowl water tank 400, and setting an initial value to operate the toilet bowl water sterilization device 10 S110.

Meanwhile, the initial value is information such as the time for operating an sterilization module 200 input by the user so as to operate or control the toilet bowl water sterilization device 10.

In the following step, the toilet bowl water sterilization device 10 radiates ultraviolet rays into the toilet bowl water tank 400 to sterilize the inside of the toilet bowl water tank 400 and toilet bowl water stored in the toilet bowl water tank 400 S120.

Meanwhile, steps of sterilizing toilet bowl water by using the ultraviolet rays may be carried out regularly according to the information (the time for operation) input by the user, or carried out continuously such that the inside of the toilet bowl water tank 400 and the toilet bowl water stored in the toilet bowl water tank 400 continue to be sterilized by means of the ultraviolet rays continuously radiated into the toilet bowl water tank 400.

In the following step, the toilet bowl water sterilization device 10 electrolyzes the toilet bowl water and converts the toilet bowl water into electrolyzed water to sterilize the toilet bowl water S130.

As described above, the step of converting the toilet bowl water into the electrolyzed water may be carried out by means of a device of aqua plasma, and the electrolyzed water has the same properties as strong alkalis or acids having strong sterilizing and cleaning abilities depending on added electrolytes.

In the following step, the toilet bowl water sterilization device 10 collects information on the state of the toilet bowl water (the number of bacteria, contamination levels, sterilization, kinds of bacteria or combination thereof) and transmit the information to the user S140.

The above-described information is output by means of LCD, LED or combination thereof provided to the toilet bowl water sterilization device 10.

Furthermore, the information is transmitted to a terminal of the user such that the user may monitor the number of bacteria, contamination levels, information on the state of sterilization or combination thereof in the toilet bowl water tank 400, anywhere and anytime the user wants.

Hereafter, as illustrated in FIG. 5, the step 120 of performing sterilization by means of ultraviolet rays and the step 130 of performing sterilization by using electrolyzed water will be described in detail by reference to FIGS. 6 and 7 respectively.

Figure 6:
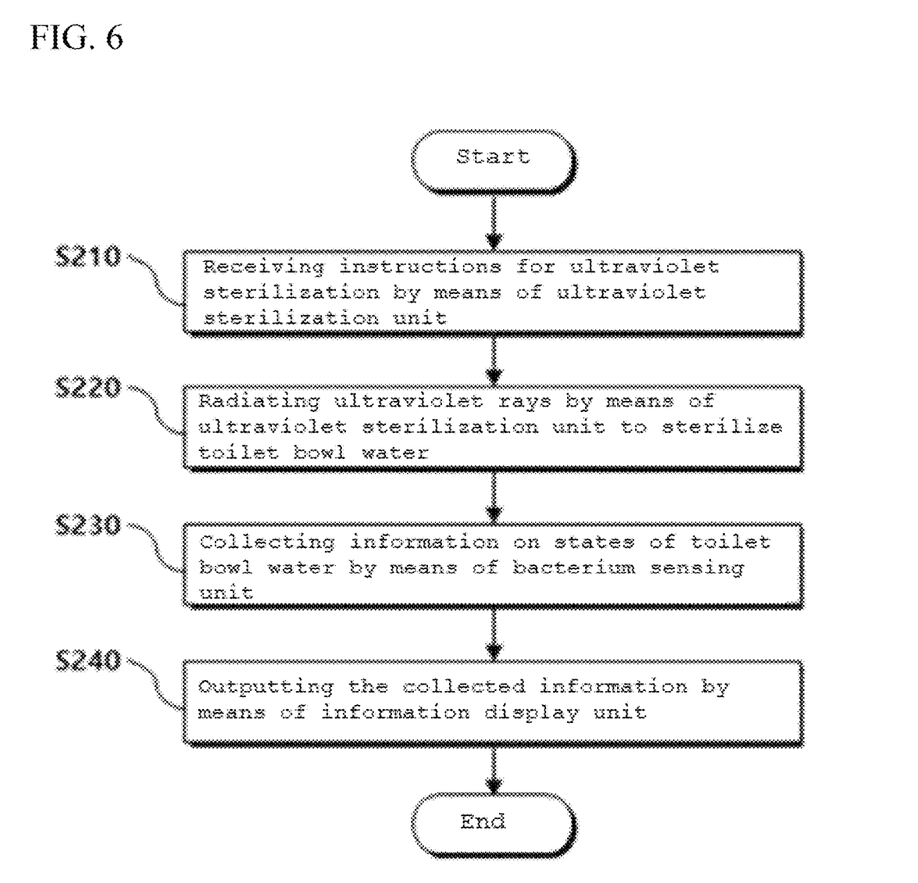
FIG. 6 is a flow chart illustrating steps of sterilizing toilet bowl water by means of ultraviolet rays according to one embodiment of the present invention.

FIG. 6 is a flow chart illustrating steps of sterilizing toilet bowl water by using ultraviolet rays according to one embodiment of the present invention.

As illustrated in FIG. 6, in the step of performing sterilization by means of ultraviolet rays, when an ultraviolet sterilization unit 210 receives the instructions for ultraviolet sterilization from the control module 100 S210, the ultraviolet sterilization unit 220 radiates ultraviolet rays having a specific range of wavelengths into the toilet bowl water tank 400 to sterilize the toilet bowl water and the inside of the toilet bowl water tank 400 S220.

Meanwhile, the instructions for the ultraviolet sterilization transmitted by the control module 100 is given directly by the user when the user remotely controls the toilet bowl water sterilization device 10 by means of the user's terminal, given regularly according to the time for operation set by the user by means of an information input unit 130, or given in real time so as to be transmitted to the ultraviolet sterilization unit 210.

The ultraviolet sterilization unit 210 radiates the ultraviolet rays by means of at least one or more of an ultraviolet sterilizer lamp, and the ultraviolet rays preferably have wavelengths of 265 nm or 253.7 nm but may have wavelengths ranging from 200 nm to 280 nm.

In the following step, the information on the state of the toilet bowl water sterilized in the ultraviolet sterilization unit 210 is collected by means of a bacterium sensing unit 240 S230.

The information includes the number of bacteria existing in the toilet bowl water, contamination levels of the toilet bowl water, the state of sterilization or combination thereof and is collected in real time or regularly. Furthermore, the collected information is transmitted to the control module 100 so as to be provided to the user.

In the following step, the information on the state of the toilet bowl water collected by the bacterium sensing unit 240 is displayed in LCD, LED or combination thereof by means of an information display unit 120 S240.

Meanwhile, the control module 100 transmits the above-described information to the user's terminal which is wired or wireless by means of the communication interface unit 150. The information may be transmitted regularly or in real time according to the conditions set by the user.

Figure 7:
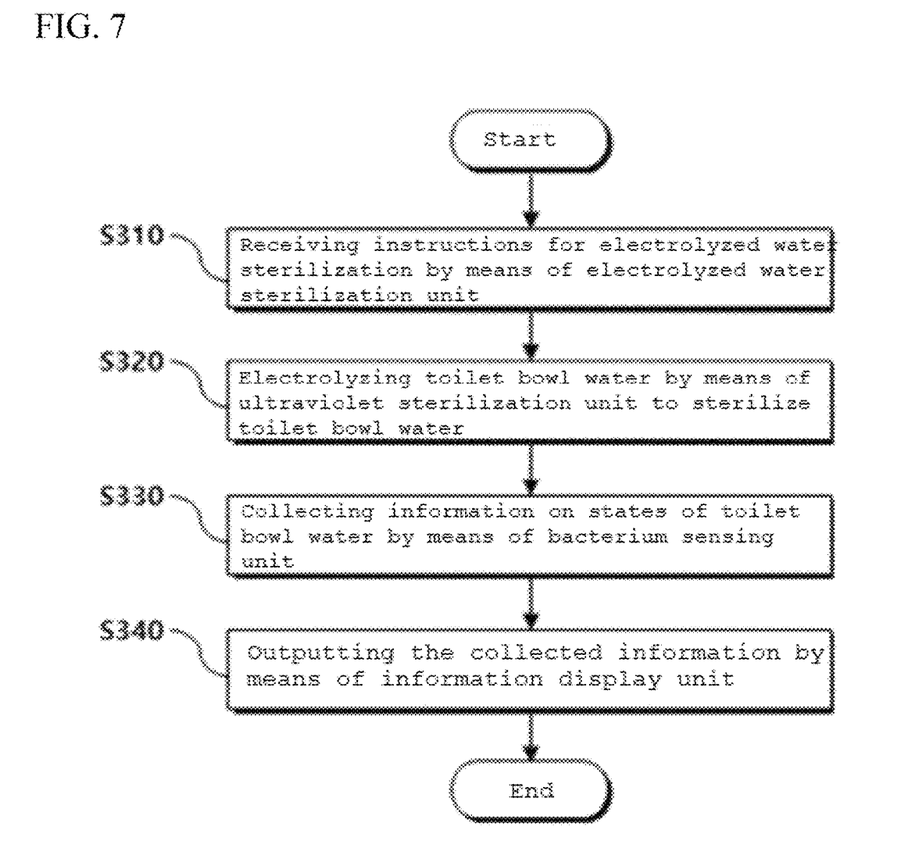
FIG. 7 is a flow chart illustrating steps of sterilizing toilet bowl water by means of electrolysis according to one embodiment of the present invention.

FIG. 7 is a flow chart illustrating steps of sterilizing toilet bowl water by means of electrolysis according to one embodiment of the present invention.

As illustrated in FIG. 7, in the step of performing sterilization by electrolyzing toilet bowl water stored in the toilet bowl water tank 400, when the instructions for electrolyzed water sterilization is received from the control module 100 by means of an electrolyzed water sterilization unit 220 S310, the electrolyzed water sterilization unit 220 electrolyzes the toilet bowl water stored in the toilet bowl water tank 400 to sterilize the toilet bowl water S320.

Then, the electrolysis is preferably performed according to a preset time for operation but may be performed by the user when the user remotely controls the toilet bowl water sterilization device 10 by means of the user's terminal, and electrolytes provided by an electrolyte supply unit 230 may enhance the efficiency of the electrolysis.

In the following step, the information on the current state of the toilet bowl water is collected by means of the bacterium sensing unit 240 S330, and the collected information is displayed in LCD, LED or combination thereof by means of the information display unit 120 such that the user may instantly recognize the information S340.

By reference to FIGS. 6 and 7, the steps of sterilizing toilet bowl water have been separately described in detail, but the above-described steps of sterilization using the ultraviolet rays and the electrolyzed water are not carried out consecutively but carried out simultaneously or independently.

Further, even when the user flushes the toilet bowl after urination and defecation, the toilet bowl may be sterilized and cleaned by the electrolyzed water. Meanwhile, as a certain amount of the toilet bowl water stagnates in the toilet bowl when the toilet bowl flushes, the toilet bowl water sterilization device 10 emits the electrolyzed water regularly to the toilet bowl to prevent bacteria from breeding in the toilet bowl.

Furthermore, the above-described steps of sterilizing toilet bowl water are continuously carried out except when the toilet bowl water sterilization device 10 stops operating due to a power outage or other external factors, such that the user may be provided with an environment that is pleasant and clean.

As described above, a toilet bowl water sterilization device and method thereof according to the present invention are effective in electrolyzing toilet bowl water where bacteria often breed, converting the toilet bowl water into sterilizing water having sterilizing and cleaning abilities to sterilize bacteria existing in the toilet bowl water as well as a toilet bowl water tank and a toilet bowl without using a cleaning agent or other chemical substances.

While the present invention has been described in connection with the preferred embodiments of the present invention, it is to be understood that the technical spirit of the present invention is not limited to the described embodiments and that each components of the present invention may be changed or modified within the technical scope of the present invention for the achievement of the same purposes and effects.

Although the present invention has been illustrated and described in relation to the preferred embodiments, it is not limited to the embodiments described above. It is to be understood that various modifications and equivalent arrangements of the embodiments may be made by those skilled in the art to which the present invention pertains without departing from the spirit and scope of the present invention claimed in the appended claims and should be included within the spirit and scope of the present invention.

The present invention is capable of sterilizing and cleaning a toilet bowl water tank and a toilet bowl without using cleaning agents for toilet bowls, a chemical compound, by electrolyzing toilet bowl water where bacteria often breed and converting the toilet bowl water into sterilizing water having sterilizing and cleaning abilities.

The invention claimed is:

1. A toilet bowl water sterilization device comprising:
   an electrolyzed water sterilization unit for converting water in a water tank of a toilet bowl into electrolyzed water by electrolysis so as to sterilize the water in the water tank, wherein the toilet bowl includes a urinal, a closet bowl, a water closet or a bidet; and a control module for controlling the electrolyzed water sterilization unit, wherein the control module is configured to set conditions for converting the water into the electrolyzed water, control an operation of sterilizing the water in the water tank, monitor a state of the water in the water tank, or perform combination thereof.

2. The toilet bowl water sterilization device according to claim 1, wherein the electrolyzed water sterilization unit is configured to add electrolytes to convert the water into the electrolyzed water, wherein the electrolytes include salt, potassium or combination thereof, and wherein the electrolytes are added inside the water tank, added through a tap water pipe for providing water into the water tank, or added through link thereof.

3. The toilet bowl water sterilization device according to claim 1, wherein the toilet bowl water sterilization device further comprises an ultraviolet sterilization unit for radiating ultraviolet rays into the water tank to sterilize the water in the water tank.

4. The toilet bowl water sterilization device according to claim 1, wherein the electrolyzed water sterilization unit further includes an aqua plasma device, wherein the aqua plasma device sterilizes the water in the water tank using a catalyst.

5. The toilet bowl water sterilization device according to claim 1, wherein the toilet bowl water sterilization device further comprises a bacterium sensing unit for sensing bacteria in the water in the water tank and for collecting information on a state of the water in the water tank including kinds of bacteria, a number of bacteria, levels of contamination of the water in the water tank, whether sterilization is performed or not, or combination thereof to provide the information on the state of the water in the water tank to the control module.

6. The toilet bowl water sterilization device according to claim 1, wherein the control module further comprises an information display unit for displaying a state where the toilet bowl water sterilization device operates, information on a state of the water, or combination thereof.

7. The toilet bowl water sterilization device according to claim 1, wherein the control module further comprises a communication interface unit for wired communication, wireless communication, or a combination thereof to transmit information on a state of the water in the water tank to a user's terminal, or to control operation of the toilet bowl water sterilization device from the user's terminal.

8. A method of sterilizing toilet bowl water comprising:
control steps of setting conditions for converting water in a water tank of a toilet bowl into electrolyzed water by electrolysis, wherein the toilet bowl includes a urinal, a closet bowl, a water closet or a bidet controlling an operation of sterilizing the water in the water tank, monitoring a state of the toilet bowl water, or performing combination thereof; and sterilization steps of converting the water in the water tank into electrolyzed water for sterilizing the water in the water tank.

9. The method of sterilizing toilet bowl water according to claim 8, wherein the converting the water in the water tank into the electrolyzed water includes adding electrolytes including salt, potassium or combination thereof to the water in the water tank, and
wherein the electrolytes are added inside the water tank, added through a tap water pipe providing water into the water tank, or added through link thereof.

10. The method of sterilizing toilet bowl water according to claim 8, wherein the sterilization steps further comprises sterilizing the water in the water tank by an ultraviolet sterilization unit radiating ultraviolet rays or sterilizing the water in the water tank by an aqua plasma device using a catalyst.

11. The method of sterilizing toilet bowl water according to claim 8, wherein the method of sterilizing toilet bowl water further comprises a bacterium sensing step, whereby the bacterium sensing step comprises collecting information on a state of the water in the water tank including kinds of bacteria, a number of bacteria, levels of contamination of the water, whether sterilization is performed or not, or combination thereof and transmitting the information to user's terminal.

12. The method of sterilizing toilet bowl water according to claim 8, wherein the method of sterilizing toilet bowl water further comprises an information display step to display operational location of the toilet bowl water sterilization device, information collected on the toilet bowl water, or combination thereof.

* * * * *